United States Patent [19]

Murphy

[11] Patent Number: 5,569,579
[45] Date of Patent: Oct. 29, 1996

[54] SYNTHETIC-BASED PLATELET STORAGE MEDIA

[75] Inventor: Scott Murphy, Ardmore, Pa.

[73] Assignee: Thomas Jefferson University, Philadelphia, Pa.

[21] Appl. No.: 210,033

[22] Filed: Mar. 17, 1994

Related U.S. Application Data

[63] Continuation-in-part of Ser. No. 984,272, Dec. 1, 1992, Pat. No. 5,376,524, which is a continuation of Ser. No. 678,699, Apr. 1, 1991, abandoned.

[51] Int. Cl.$^6$ ..................................................... A01N 1/02
[52] U.S. Cl. ............................ 435/2; 424/532; 435/240.1
[58] Field of Search ...................... 435/2, 240.1; 424/532

[56] References Cited

U.S. PATENT DOCUMENTS

| | | | |
|---|---|---|---|
| Re. 32,874 | 2/1989 | Rock et al. | 424/101 |
| 4,390,619 | 6/1983 | Harmening-Pittiglio | 435/2 |
| 4,447,415 | 5/1984 | Rock et al. | 424/101 |
| 4,695,460 | 9/1987 | Holme et al. | 424/101 |
| 5,043,261 | 8/1991 | Goodrich et al. | 435/2 |
| 5,178,884 | 1/1993 | Goodrich et al. | 424/533 |
| 5,213,814 | 5/1993 | Goodrich, Jr. et al. | 424/532 |
| 5,328,844 | 7/1994 | Moore | 435/240.31 |

OTHER PUBLICATIONS

Gibco Catalog p. 101 (1990).
Murphy S et al, Transfusion 31:16–20 (1991).
Lewandowski et al, Am. J. Physiol. 261: H354–63 (1991).
Grant & Hackh's Chemical Dictionary p. 102 (1969).
Biochemistry, Albert L. Lehninger p. 1991 (1970).
Shimizu et al.; Roles of acetate and phosphate in successful storage of platelet concentrates prepared with and acetate-containing additive solution; Transfusion, vol. 33, No. 4— 1993; pp. 304–309.
Beutler, Ernest, MD; Artificial preservative for platelets; Transfusion, vol. 33, No. 4— 1993; pp. 279–280.
Whisson et al.; Quantitative study of starving platelets in a minimal medium; maintenance by acetate or plasma but not by glucose; Transfusion Medicine, 1993, 3; pgs.
Shimizu et al.; First Autoclave–Sterilized Platelet–Additive Solution Containing Glucose with a Physiological pH for the Preparation of Plasma–Poor Platelet Concentrates; Vox Sang 1992; 62:87–93.
Shimizu et al.; Plasma–Depleted Platelet Concentrates Prepared with a New Washing Solution; Vox Sang 1993; 64:19–23.
Gulliksson et al.; Storage of platelets in additive solutions: a new method for storage using sodium chloride solution; Transfusion vol. 32, No. 5 — 1992; pp. 435–440.

Bertolini et al.; Platelet Concentrates Stored in Synthetic Medium after Filtration; Vox Sang 1992; 62:82–86.
Holme et al.; Improved maintenance of platelet in vivo viability during storage when using a synthetic medium with inhibitors; J. Lab Clin Med Feb. 1992; pp. 144–150.
Gulliksson, H.; Storage of platelets in additive solutions: the effect of citrate and acetate in in vitro studies; Transfusion 1993— vol. 33, No. 4.; pp. 301–303.
Gulliksson et al.; Storage of platelets in additive solutions: a new method for Storage using sodium chloride solution; Transfusion 1992; 32: 435–440.
Bertolini, et al.; Platelet quality after 15–day storage of platelet concentrates prepared from buffy coats and stored in a glucose–free crystalloid medium; Transfusion 1992— vol. 32, No. 1; pp. 9–16.
Cesar, et al.; Plasma Free Fatty Acid metabolism During Storage of Platelet Concentrates for Transfusion; Transfusion 27 (5): 434–437 (1987).
Kilkson et al.; Platelet Metabolism During Storage of Platelet Concentrates at 22° C.; Blood 64(2): 406–414 (1984).
Murphy; Platelet Transfusion; Progress in Hemostasis and Thrombosis; vol. III, Ed. by T. Spaet et al. (1976).
Murphy et al.; Platelet Storage at 22°C.; Role of Gas Transfusion in a New Container; Blood 60(1): 194–200 (1982).
Murphy; Platelet Storage for Transfusion; Seminars on Hematology 22(3): 165–177 (1985).
Murphy; The Preparation and Storage of Platelets for Transfusion; Mammon et al. Publications, Ltd., 1980.
Shimizu et al.; Plasma–Poor Platelet Concentrates (PC) Prepared By Autoclave–Sterilized Additive Solution Containing Glucose With Physiological pH; Abstract, Nov. 10–15 1990, meeting of Amer. Assoc. Blood Banks, Los Angeles, Ca.
Simon et al.; Extension of Platelet Concentrate Storage; Transfusion 23: 207–212 (1983).

*Primary Examiner*—David M. Naff
*Assistant Examiner*—Sandra Saucier
*Attorney, Agent, or Firm*—Woodcock Washburn Kurtz MacKiewicz & Norris

[57] ABSTRACT

Synthetic-based platelet storage media are provided along with methods of using the media for the storage of platelets for an extended period of time. The synthetic-based media contain phosphate and a substrate for oxidative phosphorylation and for providing buffering in the media upon oxidation selected from the group including pyruvate, butyrate, $C_{3-8}$ fatty acid anions, acetate, acetoacetate, acetone, and beta-hydroxybutyrate.

8 Claims, No Drawings

SYNTHETIC-BASED PLATELET STORAGE MEDIA

Portions of this invention may have been supported by a United States Government agency grant provided by the National Institute of Health, grant NIH HL 20818.

This application is a continuation-in-part of application Ser. No. 984,272 filed Dec. 1, 1992, now U.S. Pat. No. 5,376,524, which is a continuation of application Ser. No. 678,699 filed Apr. 1, 1991, now abandoned, both of which are incorporated herein in their entireties.

FIELD OF THE INVENTION

The present invention relates to the storage of human platelets in a synthetic-based storage medium. Specifically, the invention relates to the storage of platelets in an aqueous electrolytic solution in contrast to plasma-based storage media.

BACKGROUND OF THE INVENTION

A great deal is known about human platelet cells. General publications describing techniques, materials, and methods for the storage of platelets are described by Murphy et al. in "Improved Storage of Platelets for Transfusion in a New Container", Blood 60(1):194–200 (1982); by Murphy in "The Preparation and Storage of Platelets for Transfusion", Mammon, Barnhart, Lusher, and Walsh, PJD Publications, Ltd., Westbury, N.Y. (1980); by Murphy in "Platelet Transfusion", Progress in Hemostasis and Thrombosis, Vol. III, Ed. by T. Spaet, Grune and Stratton, Inc. (1976); by Murphy et al. in "Platelet Storage at 22° C.: Role of Gas Transport Across Plastic Containers in Maintenance of Viability", Blood 46(2): 209–218 (1975); by Kilkson, Holme, and Murphy in "Platelet Metabolism During Storage of Platelet Concentrates at 22° C., Blood 64(2):406–414 (1984); by Murphy in "Platelet Storage for Transfusion", Seminars in Hematology 22(3): 165–177 (1985); by Simon, Nelson, Carmen, and Murphy in "Extension of Platelet Concentrate Storage", Transfusion 23:207–212 (1983); by Cesar, Diminno, Alam, Silver, and Murphy in "Plasma Free Fatty Acid Metabolism During Storage of Platelet Concentrates for Transfusion", Transfusion 27(5): 434–437 (1987), each of which publications is hereby incorporated by reference as if more fully set forth herein.

In order to maintain viability, platelets must generate new adenosine triphosphate (ATP) continuously to meet their energy needs. Two chemical pathways are generally available: glycolysis and oxidative phosphorylation. In glycolysis, one molecule of glucose is converted to two molecules of lactic acid generating two molecules of ATP. In oxidation, glucose, fatty acid or amino acid enters the citric acid cycle and is converted to $CO_2$ and water. This pathway requires the presence of an adequate supply of oxygen. It is much more efficient than glycolysis, producing 36 molecules of ATP per molecule of glucose.

It has been recognized that platelets will meet their energy needs in a manner which is not necessarily consistent with their long term storage ex vivo in a viable condition. When given adequate oxygen, platelets produce most of their required ATP through oxidation, but continue to produce lactic acid through glycolysis instead of diverting all metabolized glucose through the oxidative pathway. Therefore, during storage of platelets in plasma, a glucose-containing medium, lactic acid concentrations have been found to rise approximately 2.5 mM per day. This leads to a gradual fall in pH, even in the presence of naturally occurring plasma buffers, principally sodium bicarbonate.

A considerable body of prior art exists concerning storage of platelets. Prior work has shown that the duration of platelet storage is limited by the continuing production of lactic acid by platelets. Although this provides energy for the platelets, the lactic acid produced acidifies the medium containing the platelets, which eventually destroys the cells. It is also known that fatty acids and amino acids may be used as substrates for oxidative metabolism of stored platelet cells.

In routine blood banking practice, platelet concentrates (PC) are prepared by drawing a unit of blood (about 450 ml) into a plastic bag containing an anticoagulant and then centrifuging the blood into three fractions: red cells, plasma, and platelets. The separated platelet fraction is then suspended in approximately 50 ml of plasma. This platelet-containing product is then stored until needed for transfusion into a patient. New techniques for preparing platelets for transfusion include platelet pheresis and the "buffy coat technique". During platelet pheresis, a single donor provides about five units of platelets by allowing the blood to be withdrawn and processed by a pheresis machine which separates the platelets for storage and redirects plasma, and optionally also the red cells, back to the donor. The "buffy coat technique" allows for the pooling of the platelets from several donors, usually about 4–6 donors, with storage of the platelets in a mixture of plasma and synthetic medium.

A number of interrelated factors have been shown to affect platelet viability and function during storage. For example, the anticoagulant used for blood collection, the method used to prepare PC, and the type of storage container used.

The currently accepted standard practice is to store PC for five days at 22° C.; after five days, it has been shown that platelet function may be impaired. In addition to storage time, other storage conditions have been shown to affect platelet metabolism and function including initial pH, storage temperature, total platelet count, plasma volume, and agitation during storage.

One of the major problems in PC storage is regulation of pH. Virtually all units of PC show a decrease in pH from their initial value of approximately 7.0. This decrease is primarily due to the production of lactic acid by platelet glycolysis and to a lesser extent to accumulation of $CO_2$ from oxidative phosphorylation. As the pH falls, the platelets change shape from discs to spheres. If the pH falls below 6.0, irreversible changes in platelet morphology and physiology render them nonviable after transfusion. An important goal in platelet preservation, therefore, is to prevent this decrease in pH. Platelets must be stored in a container permeable to oxygen since glycolysis is stimulated when oxygen availability is limited.

In association with the decrease in pH, striking decreases in the total amount of ATP per platelet have been observed. It is well known that this reduction of the total ATP level is, in part, secondary to the degradation of metabolic ATP to hypoxanthine. The depletion of metabolically available ATP affects platelet function because ATP is essential for such roles in hemostasis as platelet adhesion and platelet aggregation. The ability of PC to maintain total ATP at close to normal levels has been found to be associated with platelet viability.

The composition of platelet storage media has been shown to have a direct effect on the maintenance of platelet function and viability. A number of approaches for the storage of platelets for transfusion have been described.

U.S. Pat. No. 2,786,014 (Tullis) discloses a therapeutic product for injection into humans comprising gelatin, sodium chloride, sodium acetate, carbohydrate (glucose), platelets, and water. It is taught at Col. 2, line 56–62, that the acetate anion acts as an antiagglutinate for the platelets in this composition. The glucose is disclosed as an example of a hypertonicity-increasing agent.

Re 32,874 (Rock et al.) and U.S. Pat. No. 4,447,415 (Rock et al.) disclose a medium for storing platelets in a plasma-free, balanced salt medium. Various additional additives may be added to enhance platelet stability including nutrients, reversible inhibitors of platelet activation, substances to raise cyclic adenosine monophosphate levels, and buffering agents. The disclosed nutrients are fructose, adenine, or acetyl CoA. The reversible inhibitors include indomethacin, quinacrine, or vitamin E. Prostaglandins E1, D2, or I2 are taught for raising AMP levels. The buffering agents disclosed are phosphate or amino acids such as histidine, cysteine, tyrosine, lysine or arginine.

U.S. Pat. No. 4,390,619 (Harmening-Pittiglio) discloses a method of storing and preserving shelf life of platelets for transfusion using ion-exchange resins. These resins provide a source of metabolizing ions in an amount and at a rate sufficient to maintain both pH and ATP levels suitable for transfusion.

Shimizu et al., "Plasma-poor Platelet Concentrates (PC) Prepared by Autoclave-Sterilized Additive Solution Containing Glucose With Physiological pH" (1990) sets forth a synthetic storage medium containing added glucose, maltose, phosphate, and acetate wherein the amount of phosphate and acetate is above 20 mM.

A need exists in the area of synthetic blood platelet storage media to further understand the interactions between the additives used to extend platelet storage and to determine which additives factor in significantly to the maintenance of pH and which additives can be deleted.

SUMMARY OF THE INVENTION

Synthetic-based media for the storage of platelets are set forth containing phosphate and a substrate for oxidative phosphorylation and for providing buffering in the media upon their oxidation. The substrate agents are present in the media in their solubilized state and include the compounds acetone, acetoacetate, beta-hydroxybutyrate, butyrate, $C_{3-8}$ fatty acid anions, and pyruvate. The substrate agents are generally presented as acetone and salts of acetate, acetoacetate, beta-hydroxybutyrate, butyric acid, $C_{3-8}$ fatty acids, and pyruvic acid. The substrate agent is preferably presented in a physiologically acceptable form and generally as either the sodium, lithium, or potassium salt. The synthetic-based media preferably contains a sugar capable of promoting the formation of adenosine triphosphate. The synthetic-based media contains an aqueous electrolyte solution for suspending the blood platelets in a physiologically acceptable suspension.

The synthetic-based media are used to extend the storage life of blood platelets, in the absence of a substantial amount of plasma. The synthetic-based medium is added to a platelet composition containing platelets and residual amounts of plasma and anticoagulant to form the storage composition using conventional storage techniques. The stored compositions can then be used for transfusion, preferably without the need for any intermediate washing prior to transfusion.

DETAILED DESCRIPTION OF THE INVENTION

The present invention provides synthetic media for the storage of human blood platelets and also methods for storing those platelets in the synthetic media. As commonly known, platelets are either stored in plasma or in a synthetic media which is generally a physiologically compatible, aqueous electrolyte solution. These storage media also may contain various additives to prolong the storage life of the platelets. The present invention relates to synthetic media which, prior to being admixed with the platelets and associated plasma and anticoagulant, is essentially plasma-free in that it contains preferably no additional plasma, or at least less than 20% by volume, more preferably less than 5% by volume, plasma.

The use of the term "synthetic" with regard to the final platelet storage composition set forth herein, which contain the synthetic storage medium, the platelets, and associated plasma and anticoagulant, refers to a composition that contains less than 50% by volume plasma. The final synthetic platelet storage composition preferably contains less than about 35%, preferably less than about 30%, more preferably less than 25%, and even more preferably less than 20%, by volume plasma. Although varying due to the level of plasma extraction, typical final platelet storage compositions of the present invention contain from at least about 60%, preferably at least about 65%, more preferably at least about 70%, and even more preferably at least about 80%, by volume of the synthetic media, which contains the electrolytic solution, phosphate, and organic buffering compounds. Such synthetic media platelet compositions are referred to as being essentially plasma free.

The synthetic media of the present invention includes a physiologically compatible, aqueous electrolytic solution. Such solutions are generally known, see e.g. U.S. Pat. No. 4,695,460 and U.S. Pat. No. Re. 32,874, which are both incorporated herein in their entirety, and contain such ionic elements in solution as sodium, potassium, magnesium, chloride, and calcium. These solutions may also contain bicarbonate and citrate ions, generally added as their sodium salts, and various other compounds. Commercially available base solutions include Ringer's solution (Baxter Healthcare, Deerfield, Ill.). The electrolytic solution generally constitutes at least about 80%, preferably at least about 90%, and more preferably at least about 95%, by weight of the synthetic media.

The physiologically compatible, aqueous electrolytic solutions useful in the present invention can be varied with only marginal effect on the storage capacity of the final platelet composition. Those of skill in the art are well versed in the various commercially available electrolytic solutions. The electrolytes are contained in the solution in amounts such that when added to the platelets the final composition contains the electrolytes in the approximate concentrations found in normal blood plasma. The electrolytes most commonly employed include sodium chloride, potassium chloride, calcium chloride, and magnesium sulphate, among others. Citrate, added generally as sodium citrate, is useful as an anticoagulant for the platelets. Generally ranges for the various individual ionic species in the electrolytic solution are set forth in Table I.

TABLE I

| Ionic Species | Concentration (mM) | |
| --- | --- | --- |
| | Broad | Narrow |
| Na | 125–250 | 160–215 |
| Cl | 50–150 | 75–125 |
| K | 1.5–7 | 2.5–5.5 |

TABLE I-continued

| | Concentration (mM) | |
|---|---|---|
| Ionic Species | Broad | Narrow |
| Citrate | 5–30 | 13–20 |
| Mg | 0.2–2 | 0.25–1 |
| Ca | 0–3 | 1–2.5 |

The electrolytic solution can further contain such compounds as bicarbonate, generally from about 20–50 mM, and sulphate, generally from about 0.5–2.5 mM.

The synthetic media of the present invention are formulated with the addition of phosphate along with organic buffering compounds that act as substrates for oxidative phosphorylation and also for providing buffering in the medium during platelet storage. These organic buffering compounds are thought to consume a hydrogen ion during their oxidative metabolism during platelet storage and thus act to counterbalance the noticed pH fall due to the production of lactic acid. Such organic buffering compounds include acetate, acetone, pyruvate anion, butyrate anion, $C_{3-8}$ fatty acid anions, and ketone body anions such as acetoacetate and beta-hydroxybutyrate. The preferred organic components are pyruvate and acetate. The anions are supplied to the synthetic media in a physiologically acceptable form, such as the sodium, lithium, or potassium salt, or the acid itself.

Phosphate is presented in an amount such that the concentration of phosphate in the final platelet composition is from about 1–40 mM, preferably about 1–20 mM, more preferably from about 5–15 mM, and even more preferably from about 10–15 mM. Phosphate is preferably presented along with the electrolytic solution as part of the synthetic medium in concentrations of from about 1–80 mM, generally from about 1–60 mM, and in some cases from about 1–40 mM. The phosphate is thought to inhibit AMP deaminase, which is activated upon a rise in AMP when ATP reacts with the compounds that can be metabolized by oxidative phosphorylation. The rise in AMP deaminase leads to depletion of cellular adenine nucleotides which may lead to irreversible cellular damage and acceleration of lactic acid production to compensate for the decrease in ATP. The presence of phosphate thus counteracts any detrimental side reactions that may occur in the media due to the presence of the organic buffering compounds that can be metabolized by oxidative phosphorylation. It is also believed that phosphate provides buffering necessary during the phase of initial preparation. Phosphate ion is generally added as a commercially available sodium salt, sodium phosphate USP from American Reagent Laboratories, Inc., which is a mixture of $Na_2HPO_4$ and $NaH_2PO_4$.

The organic buffering compounds are presented in an amount such that their individual final concentration in the platelet composition is from about 1–40 mM, preferably from about 1–20 mM, more preferably from about 5–15 mM, and even more preferably from about 10–15 mM. Again, the organic buffering compounds are preferably presented along with the electrolytic solution as part of the synthetic medium in concentrations of from about 1–80 mM, generally from about 1–60 mM, and in some cases from about 1–40 mM.

The synthetic media are preferably prepared by adding the stated amount of phosphate and organic buffering compound of this invention with the base aqueous electrolyte solution. The base solution will preferably also include an effective amount of a sugar capable of promoting the formation of adenosine triphosphate in the storage of platelets. Such sugars include glucose or dextrose ($C_6H_{12}O_6$), fructose, mannose, sucrose, and maltose, preferably glucose. The sugars are presented in typical amounts such that the concentration of the sugar in the platelet composition is from about 5–40 mM, preferably about 10–15 mM. Thus, the sugar is generally presented within the synthetic media in a concentration of from about 5–80 mM, generally from about 5–60 mM, and in some cases from about 5–40 mM. The base solution will preferably be essentially free of other compounds, that is, compounds other than the stated electrolytic ions, sugars for ATP formation, or the prescribed amounts of phosphate and organic buffering compounds. The pH of the synthetic media is preferably from about 6.5 to 7.5, preferably from about 6.8–7.2, and more preferably about 7, and the osmolarity is from about 200 to about 400, preferably from about 250 to about 350, and more preferably about 300 milliOsm.

The processes for the storage of platelets in the synthetic media is effected by conventional techniques. Generally, the blood sample, typically a unit of blood (450 ml), maintained in a plastic bag with anticoagulant, is centrifuged or otherwise processed to provide three fractions: red cells, plasma, and platelets. Anticoagulants are known by those of skill in the art, as shown by U.S. Pat. No. 4,695,460, which is incorporated herein in its entirety. The platelet fraction is then recovered with the removal of plasma, however, as noted above, residual plasma may be retained with the platelets. The platelets are then suspended in the synthetic medium to an adequate volume, generally from about 40 to about 60 ml. The platelet concentrations for storage range from about $0.8 \times 10^9$ to about $2.5 \times 10^9$ platelets/ml. Additional techniques for obtaining the platelets include platelet pheresis and the "buffy coat technique".

EXAMPLE 1

Pyruvate Addition

Paired platelet storage medium compositions were prepared from whole blood donations in accordance with standard methods well known in the art, except that the supernatant plasma was extracted from the bag containing the platelet button as completely as possible using a Fenwal plasma extractor (Fenwal Laboratories, Deerfield, Ill.).

The platelets were suspended in a synthetic medium containing about 11 mM pyruvate and about 10 mM phosphate. The pyruvate was added as pyruvic acid, sodium salt form from Sigma Chemical Co. The platelets were suspended in about 60 ml of the synthetic medium and the final platelet suspension volume was about 70 ml. The mean plasma carry over was about 21±4% by volume of the final platelet suspension.

The synthetic medium had calculated concentrations as shown in Table 1.1:

TABLE 1.1

| Synthetic Medium | |
|---|---|
| Component | Concentration (mM) |
| Sodium | 185.7 |
| Potassium | 4.8 |
| Calcium | 2.01 |
| Chloride | 108.1 |
| Magnesium | 0.32 |

TABLE 1.1-continued

| Synthetic Medium | |
|---|---|
| Component | Concentration (mM) |
| Glucose | 14.4 |
| Phosphate | 8.7 |
| Pyruvate | 11 |
| Citrate | 17 |

The pH of the synthetic medium prior to the addition of the platelets was about 7.0 and the osmolarity was about 300.

The storage was continued over a seven day period with conventional agitation on a tumbler. Metabolic parameters were analyzed on days 1, 5 and 7 of the storage as shown in Table 1.2. Measured variables included pH (measured at 22° C.), oxygen consumption ($O_2CON$, nanomoles/min./$10^9$ platelets), carbon dioxide pressure ($pCO_2$, mm Hg at 37° C.), bicarbonate level (mM), and lactate level (mM). The pH of the stored platelet compositions remained at 6.9 throughout the storage period. This pH maintenance was achieved although the lactate level increased steadily over the storage period.

Viability assays were also performed on the platelet storage compositions on days 1, 5 and 7 as shown in Table 1.3. The platelet count (PC) and mean platelet volume (MPV), both as a percentage of day 1 values, dispersion of the platelet size distribution (dispersion), percentage of discs by phase microscopy (% discs), and osmotic reversal reaction (Os Rev) all reflect platelet quality. These values all reflect acceptable values for platelet storage.

TABLE 1.2

| METABOLIC PARAMETERS | | | |
|---|---|---|---|
| | DAY 1 | DAY 5 | DAY 7 |
| pH | 6.995 ± .061 | 6.986 ± .069 | 6.965 ± .106 |
| $O_2CON$ | 1.00 ± .269 | 0.741 ± .221 | 0.676 ± .247 |
| $pCO_2$ | 24.2 ± 3.30 | 23.5 ± 3.92 | 21.4 ± 3.84 |
| Bicarbonate | 4.69 ± .622 | 4.30 ± .672 | 3.54 ± .752 |
| Lactate | 1.49 ± .514 | 5.12 ± 1.24 | 7.68 ± 2.26 |

TABLE 1.3

| VIABILITY ASSAYS | | | |
|---|---|---|---|
| | Day 1 | Day 5 | Day 7 |
| PC | — | 98.8 ± 3.26 | 96.0 ± 3.14 |
| MPV | — | 102.0 ± 4.81 | 106.4 ± 5.18 |
| Dispersion | 1.68 ± .051 | 1.75 ± 0.038 | 1.75 ± 0.057 |
| % Discs | 90.8 ± 5.85 | 78.3 ± 7.53 | 72.5 ± 15.8 |
| OsRev | 73.2 ± 8.67 | 55.7 ± 8.76 | 44.5 ± 5.95 |

EXAMPLE 2

Acetoacetate and Butyrate

Platelet storage media were prepared in accordance with the procedures set forth in Example 1, except that the pyruvate was replaced by acetoacetate and butyrate, respectively. The acetoacetate was added as the lithium salt form and the butyrate was added as butyric acid, sodium salt form (both from Sigma Chemicals Co.). Five platelet media were prepared using acetoacetate and four platelet media were prepared using butyrate. The initial concentration of the acetoacetate and butyrate was from about 10–15 mM for each medium.

The results of the metabolic parameters and viability assays are set forth in Tables 2.1 and 2.2, respectively. The variables are similar to those in Example 1, except that the partial pressure of oxygen ($pO_2$, mm Hg at 37° C.) is reported and the glucose level is reported in mM. The experiments extended over a seven day period and results obtained for days 3–5 were averaged as were the results for days 6–7.

TABLE 2.1

| Metabolic Parameters | | | | |
|---|---|---|---|---|
| | | DAY 1 | DAY 3–5 | DAY 6–7 |
| pH | Acetoacetate | 7.07 ± .03 | 7.05 ± .07 | 6.96 ± .10 |
| | Butyrate | 6.98 ± .03 | 6.86 ± .08 | 6.62 ± .11 |
| $pCO_2$ | Acetoacetate | 26.1 ± 3.86 | 26.8 ± 3.65 | 24.9 ± 4.13 |
| | Butyrate | 22.0 ± 1.4 | 20.2 ± .87 | 19.5 ± .79 |
| $pO_2$ | Acetoacetate | 111.8 ± 20.5 | 123.3 ± 20.8 | 137.0 ± 16.5 |
| | Butyrate | 124 ± 7.26 | 135 ± 10.2 | 148 ± 6.28 |
| Bicarbonate | Acetoacetate | 4.70 ± .75 | 4.92 ± .93 | 3.84 ± .95 |
| | Butyrate | 3.43 ± .45 | 2.27 ± .37 | 1.45 ± .26 |
| Lactate | Acetoacetate | 1.32 ± .45 | 4.63 ± 1.33 | 8.48 ± 1.52 |
| | Butyrate | 1.24 ± .23 | 4.15 ± 1.30 | 7.33 ± 1.27 |
| Glucose | Acetoacetate | 13.9 ± .45 | 12.4 ± .65 | 10.4 ± .65 |
| | Butyrate | 13.8 ± .28 | 12.1 ± .34 | 10.6 ± .61 |

TABLE 2.2

| Viability Assays | | | | |
|---|---|---|---|---|
| | | DAY 1 | DAY 3–5 | DAY 6–7 |
| PC | Acetoacetate | — | 100.2 ± 2.07 | 97.4 ± 3.51 |
| | Butyrate | — | 96.6 ± 3.73 | 96.9 ± 3.46 |
| MPV | Acetoacetate | — | 89.0 ± 8.4 | 96.6 ± 6.92 |
| | Butyrate | — | 104.0 ± 5.62 | 114.7 ± 6.4 |
| Dispersion | Acetoacetate | 1.72 ± .03 | 1.77 ± .09 | 1.72 ± .07 |
| | Butyrate | 1.74 ± .03 | 1.74 ± .03 | 1.72 ± .10 |
| % Discs | Acetoacetate | 81.0 ± 6.63 | 75.0 ± 8.94 | 68.0 ± 11.7 |
| | Butyrate | 89.8 ± 5.72 | 80.0 ± 12.3 | 61.3 ± 20.1 |
| Os Rev | Acetoacetate | 60.6 ± 8.91 | 49.4 ± 3.23 | 42.6 ± 4.23 |
| | Butyrate | 78.6 ± 12.5 | 61.9 ± 11.7 | 46.8 ± 6.63 |

What is claimed is:

1. A synthetic-based medium for the storage of platelets for intravenous transfusion to humans, consisting essentially of:

(a) a sugar capable of promoting the formation of adenosine triphosphate;

(b) from about 1 to about 80 mM phosphate;

(c) from about 1 to about 80 mM of an organic compound that acts as a substrate for oxidative phosphorylation and for providing buffering in the medium upon oxidation selected from the group consisting of acetoacetate, beta-hydroxybutyrate, pyruvate, $C_{3-8}$ fatty acid anions, acetone, and mixtures thereof; and (d) at least about 95 percent by weight of a physiologically compatible, aqueous electrolyte solution.

2. The synthetic-based medium of claim 1 wherein the phosphate is present in an amount of from about 1 to about 60 mM.

3. The synthetic-based medium of claim 2 wherein said organic compound consists of pyruvate in an amount of from about 1 to about 60 mM.

4. The synthetic-based medium of claim 3 wherein the pyruvate is present in an amount of from about 1 to about 40 mM.

5. The synthetic-based medium of claim 1 wherein the sugar consists of glucose.

6. A platelet storage composition consisting essentially of:
 (a) at least about 65 volume percent of a synthetic-based medium for the storage of platelets for intravenous transfusion to humans, said medium consisting essentially of:
   (1) a sugar capable of promoting the formation of adenosine triphosphate;
   (2) phosphate;
   (3) an organic compound that acts as a substrate for oxidative phosphorylation and for providing buffering in the medium upon oxidation selected from the group consisting of acetoacetate, beta-hydroxybutyrate, pyruvate, $C_{3-8}$ fatty acid anions, acetone, and mixtures thereof; and
   (4) at least about 95 percent by weight of a physiologically compatible, aqueous electrolyte solution;
 (b) plasma and anticoagulant, wherein the platelet storage composition comprises less than about 35 volume percent plasma; and
 (c) platelets, present in a concentration of from about $0.8-2.5 \times 10^9$ platelets/ml of said platelet storage composition,
 wherein the concentration of phosphate in the platelet storage composition is from 5 mM to 40 mM and the concentration of the organic compound in the platelet storage composition is from 5 mM to 40 mM.

7. The composition of claim 6 wherein said organic compound consists of pyruvate present in an amount of from about 5 to about 25 mM in the platelet storage composition.

8. The composition of claim 6 wherein the synthetic media constitutes at least about 70% by volume of the platelet storage composition and has an osmolarity of from about 250–350 milliOsm, and wherein the platelet storage composition comprises less than about 30% by volume of plasma.

* * * * *